US00PP09956P

United States Patent [19]

Klinger

[11] Patent Number: Plant 9,956

[45] Date of Patent: Jul. 8, 1997

[54] CALATHEA PLANT NAMED 'GA-1'

[75] Inventor: John P. Klinger, Longwood, Fla.

[73] Assignee: Garden Arts Nursery, Inc., Longwood, Fla.

[21] Appl. No.: 526,402

[22] Filed: Sep. 11, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 9,621 8/1996 Lamb ..... Plt./8.1

*Primary Examiner*—James R. Feyrer

*Attorney, Agent, or Firm*—Frank B. Robb; John H. Vynalek

[57] ABSTRACT

A Calathea plant named 'GA-1' having dark green round leaves bordered with a distinctive broad metallic silver band which is often variably tinged with pink.

2 Drawing Sheets

This present invention relates to a new and distinct cultivar of Calathea, botanically known as *Calathea roseo picta,* and referred to by the cultivar name, 'GA-1 '.

The new cultivar is a mutuation discovered in Longwood, Fla. The cultivar was discovered and selected by the inventor from tissue culture derived *C. roseo picta* in Apopka, Fla. Propagation by tissue culture and division done by the inventor in Apopka, Fla. was used to increase the number of plants for evaluation and has demonstrated the stability of the combination of characteristics from generation to generation.

The following observations, measurements and values describe plants grown in Apopka, Fla. under greenhouse conditions which closely approximate those generally used in horticultural practice.

The following traits have been repeatedly observed to be characteristics which in combination distinguish 'GA-1' from others of the species *C. roseo picta,* and from the cultivar 'Garden Arts II' and the patented cultivar 'Rosy' disclosed in U.S. Pat. No. P.P. 8,836.

1. The plant, particularly when juvenile, produces leaves having an unusually broad marginal band of metallic silver-pink which extends to the leaf edge.

2. The center of the leaf is very dark green; the midrib is silver-green tinged with pink.

3. As the leaf matures, the quantity and intensity of the pink markings diminishes.

The leaves of the plant of this application are similar but materially distinguishable from those of *C. ellipse* U.S. Pat. No. P.P. 9,621. The band on the *C. ellipse* extends nearly to the leaf edge on juvenile plants and becomes somewhat more diffused on its border developing a dark green edge. While the leaf of the plant of this application initially has a border that is entire to its edge with a distinct red coloration. This color remains until the fourth or fifth leaf when the margin expands considerably and turns pale, but remains entire to the edge. In addition, the plant of this application shows more vigor and will finish growing quicker then *C. ellipse.*

All color references are measured against The Royal Horticultural Society color chart. Colors are approximate as color depends on horticultural practices such as light level and fertilization rate, among others, without, however any variance in genotype.

DETAILED BOTANICAL DESCRIPTION

Origin: Mutations of *Calathea roseo picta.*

Figure 1:
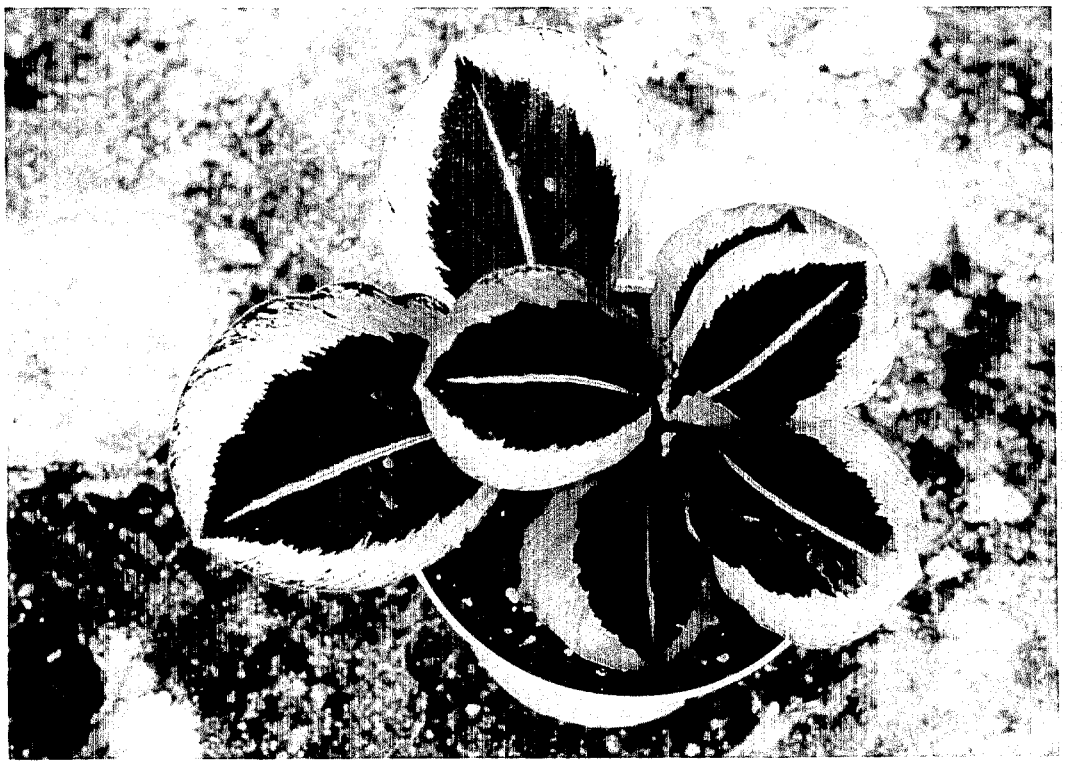
FIG. 1 is a top perspective view of a specimen of 'GA-1' in a 15.5 cm pot at approximately 24 weeks after planting an 8 week old liner obtained by tissue culture and grown under appropriate conditions.
Figure 2:
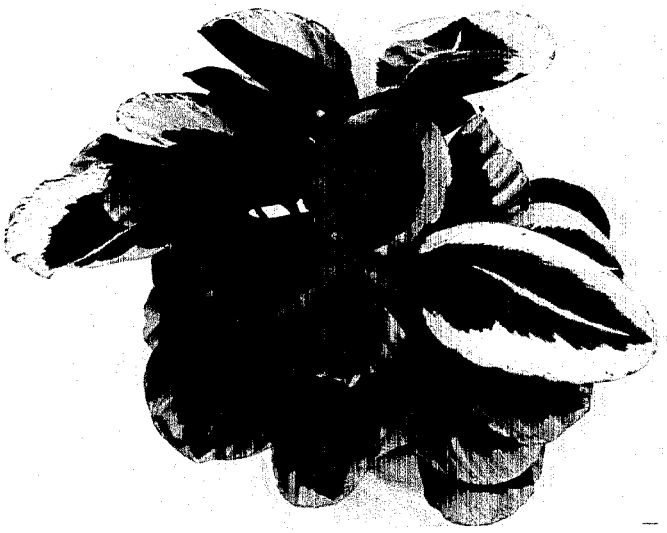
FIG. 2 shows a mature specimen of 'GA-1' and FIG. 3 shows a mature specimen of the comparison plant 'Eclipse' grown under the same conditions and of the same age. The predominant difference between these plants is in the coloring of the leaves as will be specified infra.
Figure 3:
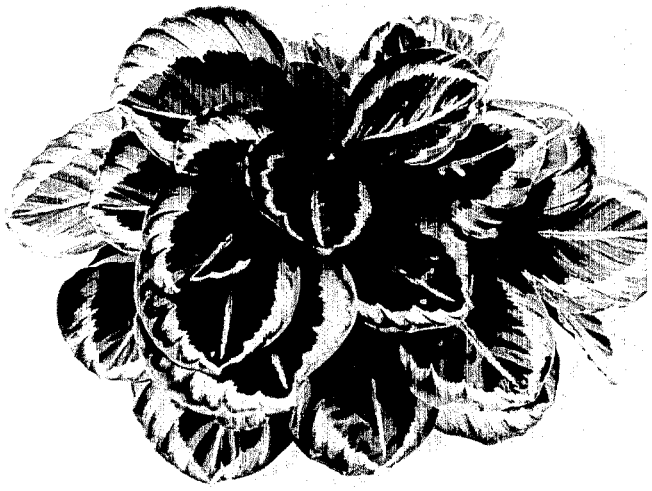

Classification: *Calathea roseo picta,* cv, 'GA-1 '.

Propagation: Asexual propagation either by tissue culture or division.

Plant: In a 15.5 cm. pot for a plant grown from an 8 week old liner after 24 weeks under appropriate growing conditions, 'GA-1' is approximately 10 cm. to 13 cm. in height and approximately 18 cm. to 21 cm. in width.

Leaves:

*Form.*—The leaf blade is orbicular with a mucronate tip and an obtuse base. The margins are entire. The midrib tends to be straight, or curved upward slightly over the length of the leaf. The leaf blade is wavy over the width of the leaf.

*Size.*—Leaf blades are approximately 9.2 cm. to 10.5 cm. in length and approximately 8.6 cm. to 9.4 cm. in width.

*Petiole.*—The petiole is approximately 5.9 cm. to 5.0 cm. in height from the base of the petiole to the base of the leaf blade on the primary shoot. Secondary shoots are somewhat smaller depending on the age of the shoot. The petiole is approximately 4 mm. in diameter just below the geniculum. The petiole below the geniculum is straight.

*Petiole wings.*—Petiole wings are approximately 4.8 cm. in length and approximately 6 mm. in width at their midpoint. The tip of the petiole wings is rounded. There is approximately 2 mm. to 6 mm. between the top of the wing and the base of the geniculum.

*Geniculum.*—The geniculum is approximately 9 mm. in length, approximately 4 mm. in diameter. The color is greener than but closest to 177 A. There is no space between the top of the geniculum and the base of the leaf blade. The geniculum is prominent. The orientation of the leaf to the petiole is variable, as the geniculum bends. During the night and early morning, the geniculum is straight and the leaf is held nearly straight above the petiole. During the day, the geniculum is bent, and the leaf is oriented approximately 90 degrees to the petiole.

*Veins.*—Veins and midrib are sunken, with the leaf blade slightly concave between veins on the upper surface. The midrib protrudes from the lower surface. Primary veins on leaves radiate out from the midrib along the length of the leaf. Veins are recessed within the leaf. There are approximately 12–14 primary veins on the leaf.

Color/pattern: The upper leaf surface is very dark green in the center, with broad marginal silver-pink bands. The leaf midrib is silver-green tinged with pink. The marginal silver bands extend to the leaf edge on juvenile plants. The quantity and intensity of the pink markings diminishes as the plant matures. Leaf top marginal edges are mottled to flecked with a discontinuous pattern of green spots. In contrast, the green-silver variegation on the top surface of leaves of 'Eclipse' contain a continuous green band at the margin.

*Upper surface.*—Margin — metallic 188 D. Leaf Center — Darker, and greener, but closest to 139 A. Midrib — Upper Surface: 59 D, outlined with metallic 194 D.

*Lower surface.*—Entirely 187 A. Midrib — Greener and redder than, but closest 177 A.

*Petiole.*—Anthocyanous 187 A.

*Petiole wing.*—Lighter than, but closest to 187 A.

Inflorescence: The inflorescence of 'GA-1' is typical of the species *Calathea roseo picta* and has no commercial significance.

Roots: Dark brown fibrous roots with fine laterals.

GENERAL OBSERVATION

A new and distinctive Calathea named 'GA-1' having very dark green round leaves bordered with a distinctive broad silver band, which is variably tinged with pink. The leaf midrib is pink and silver-green. These combined characteristics make Calathea 'GA-1' a unique new cultivar.

It is claimed:

1. A new and distinctive cultivar of Calathea plant named 'GA-1', as illustrated and described, characterized particularly as to novelty by the orbicular shape of the leaves each with a distinctive broad silver band entire to its edge, a tinge of pink being present, fading as the plant ages.

* * * * *